US012618819B2

(12) United States Patent
Sandahl et al.

(10) Patent No.: US 12,618,819 B2
(45) Date of Patent: May 5, 2026

(54) SYSTEMS AND METHODS FOR OFF-GAS DETECTION

(71) Applicant: Tyco Fire Products LP, Lansdale, PA (US)

(72) Inventors: Derek M. Sandahl, Wallace, MI (US); Alden A. Spencer, Marinette, WI (US); Kyle Moore, Marinette, WI (US)

(73) Assignee: Tyco Fire Products LP, Cranston, RI (US)

( * ) Notice: Subject to any disclaimer, the term of this patent is extended or adjusted under 35 U.S.C. 154(b) by 329 days.

(21) Appl. No.: 18/004,085

(22) PCT Filed: Sep. 28, 2021

(86) PCT No.: PCT/IB2021/058847
§ 371 (c)(1),
(2) Date: Jan. 3, 2023

(87) PCT Pub. No.: WO2022/070034
PCT Pub. Date: Apr. 7, 2022

(65) Prior Publication Data
US 2023/0280323 A1     Sep. 7, 2023

Related U.S. Application Data

(60) Provisional application No. 63/084,930, filed on Sep. 29, 2020.

(51) Int. Cl.
*G01N 33/00* (2006.01)
*A62C 3/16* (2006.01)
(Continued)

(52) U.S. Cl.
CPC .......... *G01N 33/0063* (2013.01); *A62C 3/16* (2013.01); *B60L 53/30* (2019.02); *B60L 58/10* (2019.02);
(Continued)

(58) Field of Classification Search
CPC .... G01N 33/0063; G01N 1/2226; A62C 3/16; B60L 53/30; B60L 58/10; F24F 11/33;
(Continued)

(56) References Cited

U.S. PATENT DOCUMENTS

| | | | | |
|---|---|---|---|---|
| 11,009,474 B2 * | 5/2021 | Brahem | ............. | G01N 33/0031 |
| 2007/0103325 A1 * | 5/2007 | Wagner | .................. | G08B 17/10 |
| | | | | 340/584 |

(Continued)

FOREIGN PATENT DOCUMENTS

| | | |
|---|---|---|
| CN | 110813053 A | 2/2020 |
| JP | 2011-062072 A | 3/2011 |
| KR | 10-2018-0094699 A | 8/2018 |

OTHER PUBLICATIONS

Cummings et al.; Nexceris, LLC; "Off-Gas Monitoring for Lithium Ion Battery Health and Safety"; Power Sources Committee Meeting, Wright Patterson AFB; Jun. 21, 2017; National Defense Industrial Association, https://www.ndia.org/-/media/sites/ndia/divisions/manufacturing/documents/nexceris_off-gas_monitoring.ashx; 29 pages.
(Continued)

*Primary Examiner* — Helen C Kwok
(74) *Attorney, Agent, or Firm* — Foley & Lardner LLP

(57) ABSTRACT

An off-gas detection system for mobile equipment includes an off-gas detection device, and a controller. The off-gas detection device is configured to removably couple with the mobile equipment. The off-gas detection device is configured to define a controlled flow path between an electrical energy storage device of the mobile equipment and an off-gas detector. The controller is configured to receive data from the off-gas detector regarding an air sample, determine a presence or concentration of off-gas within the air sample, and initiate one or more actions in response to determining the presence or concentration of off-gas in the air sample.

20 Claims, 4 Drawing Sheets

(51) Int. Cl.

| | |
|---|---|
| *B60L 53/30* | (2019.01) |
| *B60L 58/10* | (2019.01) |
| *F24F 7/02* | (2006.01) |
| *F24F 11/00* | (2018.01) |
| *G01K 13/00* | (2021.01) |
| *G01N 1/24* | (2006.01) |
| *G08B 17/06* | (2006.01) |
| *G08B 17/117* | (2006.01) |
| *H02J 7/65* | (2026.01) |

(52) U.S. Cl.

CPC ............ *F24F 7/02* (2013.01); *F24F 11/0001* (2013.01); *G01K 13/00* (2013.01); *G01N 1/24* (2013.01); *G08B 17/06* (2013.01); *G08B 17/117* (2013.01); *G01N 2001/245* (2013.01); *H02J 7/65* (2026.01)

(58) Field of Classification Search

CPC ....... F24F 11/0001; F24F 7/02; G08B 17/117; G08B 17/06

See application file for complete search history.

(56) References Cited

U.S. PATENT DOCUMENTS

| | | | |
|---|---|---|---|
| 2013/0175819 A1 | 7/2013 | Hindle | |
| 2013/0316198 A1 | 11/2013 | Bandhauer et al. | |
| 2014/0167694 A1* | 6/2014 | Gjinali ............... | H01M 8/04111 |
| | | | 320/109 |
| 2014/0272671 A1* | 9/2014 | Handa ....................... | B60L 3/12 |
| | | | 429/515 |
| 2018/0003685 A1* | 1/2018 | Cummings ....... | H01M 10/4228 |
| 2019/0234851 A1 | 8/2019 | Mou et al. | |
| 2020/0266405 A1* | 8/2020 | Pokora ................ | H01M 10/486 |
| 2020/0360751 A1* | 11/2020 | Ogier ..................... | A62C 37/36 |
| 2022/0401770 A1* | 12/2022 | Sandahl ............. | H01M 50/383 |
| 2022/0407174 A1* | 12/2022 | Sandahl ............. | H01M 50/249 |

OTHER PUBLICATIONS

Korean Intellectual Property Office as International Searching Authority; International Search Report and Written Opinion; International Patent Application No. PCT/IB2021/058847; Jan. 6, 2022; 8 pages.

* cited by examiner

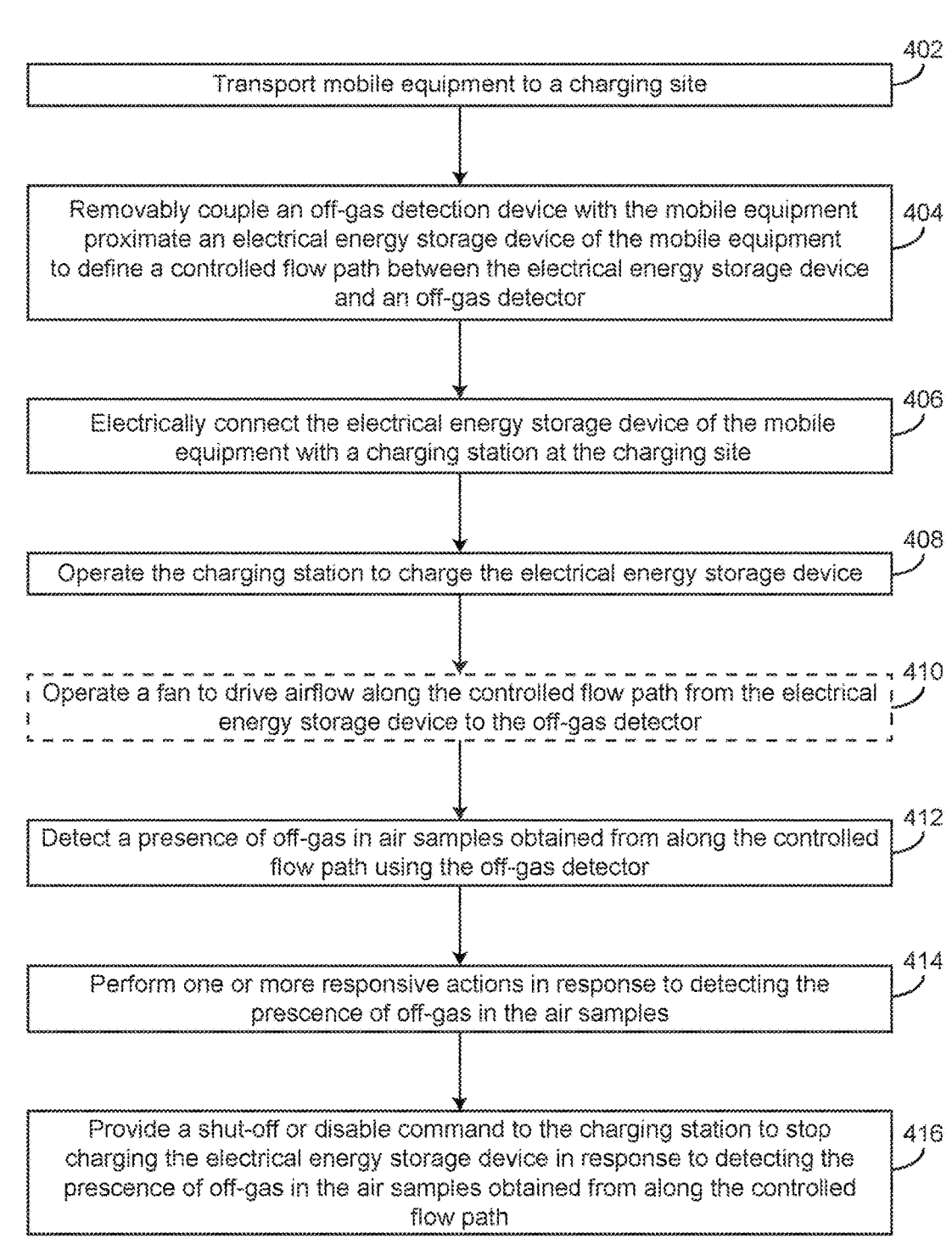

400

Transport mobile equipment to a charging site          402

Removably couple an off-gas detection device with the mobile equipment proximate an electrical energy storage device of the mobile equipment to define a controlled flow path between the electrical energy storage device and an off-gas detector          404

Electrically connect the electrical energy storage device of the mobile equipment with a charging station at the charging site          406

Operate the charging station to charge the electrical energy storage device          408

Operate a fan to drive airflow along the controlled flow path from the electrical energy storage device to the off-gas detector          410

Detect a presence of off-gas in air samples obtained from along the controlled flow path using the off-gas detector          412

Perform one or more responsive actions in response to detecting the prescence of off-gas in the air samples          414

Provide a shut-off or disable command to the charging station to stop charging the electrical energy storage device in response to detecting the prescence of off-gas in the air samples obtained from along the controlled flow path          416

FIG. 4

SYSTEMS AND METHODS FOR OFF-GAS DETECTION

CROSS-REFERENCE TO RELATED APPLICATION

This application claims the benefit of and priority to U.S. Provisional Application No. 63/084,930, filed Sep. 29, 2020, the entire disclosure of which is incorporated by reference herein.

BACKGROUND

The present disclosure relates to systems and methods for off-gas detection. More particularly, the present disclosure relates to detecting thermal runaway of batteries that are being charged by detecting off-gases.

SUMMARY

One implementation of the present disclosure is an off-gas detection system for mobile equipment, according to some embodiments. In some embodiments, the off-gas detection system includes an off-gas detection device, and a controller. In some embodiments, the off-gas detection device is configured to removably couple with the mobile equipment. In some embodiments, the off-gas detection device is configured to define a controlled flow path between an electrical energy storage device of the mobile equipment and an off-gas detector. In some embodiments, the controller is configured to receive data from the off-gas detector regarding an air sample, determine a presence or concentration of off-gas within the air sample, and initiate one or more actions in response to determining the presence or concentration of off-gas in the air sample.

In some embodiments, the off-gas detection device is removably coupled with the mobile equipment proximate the electrical energy storage device of the mobile equipment. In some embodiments, the off-gas detection system is positioned in an uncontrolled environment.

In some embodiments, the off-gas detection device further includes a fan and an electric motor. In some embodiments, the electric motor and the fan are configured to operate to draw air along the controlled flow path from the electrical energy storage device to the off-gas detector.

In some embodiments, the one or more actions include at least one of providing detection event information to a fire panel, disabling a charging operation of the electrical energy storage device, operating a ventilation system, or activating a fire suppression system. In some embodiments, the electrical energy storage device is configured to electrically couple with a charger to charge one or more battery cells of the electrical energy storage device while the off-gas detector monitors air samples from along the controlled flow path. In some embodiments, the off-gas detection device includes a hood configured to direct air from the electrical energy storage device to the off-gas detector along the controlled flow path.

Another implementation of the present disclosure is a method of detecting off-gas, according to some embodiments. In some embodiments, the method includes coupling an off-gas detection device to equipment, the equipment including an electrical energy storage device. In some embodiments, the method also includes coupling the equipment to a charging station to charge the electrical energy storage device. In some embodiments, the method also includes detecting a presence or concentration of off gas in an air sample using a controlled air path provided by the off-gas detection device, and initiating an action based on detecting the presence or concentration of the off gas.

In some embodiments, the off-gas detection device is coupled to the equipment proximate the electrical energy storage device. In some embodiments, the equipment is positioned in an uncontrolled environment and the off-gas detection device defines the controlled air path between the electrical energy storage device and an off-gas detector. In some embodiments, the method further includes operating a fan to force a flow of air along the controlled air path.

In some embodiments, the action includes at least one of providing detection event information to a fire panel, disabling a charging operation of the electrical energy storage device, operating a ventilation system, or activating a fire suppression system. In some embodiments, the equipment is at least one of a battery module on-board a vehicle, a battery module removed from a vehicle, or a mobile vehicle.

Another implementation of the present disclosure is an off-gas detection device for equipment, according to some embodiments. In some embodiments, the off-gas detection device includes an off-gas detector, and a body. In some embodiments, the body is configured to define a channel for a controlled flow path between an electrical energy storage device of the equipment and the off-gas detector. In some embodiments, the off-gas detection device is configured to removably couple with the equipment or the electrical energy storage device of the equipment so that the controlled flow path is defined between the electrical energy storage device of the equipment and the off-gas detector. In some embodiments, the off-gas detector is configured to provide sensor data to a controller for limiting charging of the electrical energy storage device in response to the sensor data.

In some embodiments, the off-gas detection device is configured to be removably coupled with the equipment proximate the electrical energy storage device of the mobile equipment. In some embodiments, the off-gas detection device further includes a fan and an electric motor. In some embodiments, the electric motor and the fan are configured to operate to draw air along the controlled flow path from the electrical energy storage device to the off-gas detector.

In some embodiments, the electrical energy storage device is configured to electrically couple with a charger to charge one or more battery cells of the electrical energy storage device while the off-gas detector monitors air samples from along the controlled flow path. In some embodiments, a connection point between the charger and the electrical energy storage device is integrated in the off-gas detection device.

In some embodiments, the off-gas detection device further includes a temperature sensor. In some embodiments, the temperature sensor is configured to monitor a temperature of the electrical energy storage device and provide the monitored temperature to the controller for use in limiting charging of the electrical energy storage device. In some embodiments, the equipment is at least one of a battery module on-board a vehicle, a battery module removed from a vehicle, or a mobile vehicle.

BRIEF DESCRIPTION OF THE DRAWINGS

The disclosure will become more fully understood from the following detailed description, taken in conjunction with the accompanying FIGURES, wherein like reference numerals refer to like elements, in which:

FIG. 4 is a flow diagram of a process for detecting off-gas or thermal runaway of one or more charging battery cells, according to some embodiments.

DETAILED DESCRIPTION

Before turning to the FIGURES, which illustrate the exemplary embodiments in detail, it should be understood that the present disclosure is not limited to the details or methodology set forth in the description or illustrated in the FIGURES. It should also be understood that the terminology used herein is for the purpose of description only and should not be regarded as limiting.

Overview

Referring generally to the FIGURES, an off-gas detection system for mobile equipment is shown. The off-gas detection system includes an off-gas detection device that can be removably coupled with the mobile equipment (e.g., proximate battery cells of the mobile equipment). The mobile equipment may be transportable between different locations (e.g., a work site, a charging site, etc.). When the mobile equipment transports to the charging site for charging, the off-gas detection device can be removably coupled to the mobile equipment. The mobile equipment can also be electrically coupled to a charging station at the charging site so that the battery cells can be recharged. The charging site may be an open or uncontrolled environment that can result in difficulty obtaining air samples for off-gas detection. When the off-gas detection device is coupled to the mobile equipment, the off-gas detection device can define a controlled flow path between battery cells of the mobile equipment and an off-gas detector external to the mobile equipment. Advantageously, this allows the off-gas detection device to be re-used for different mobile equipment and removes the need to install off-gas detectors within each mobile equipment.

The off-gas detector may obtain air samples from along the controlled flow path and provide sensor data to a controller (e.g., at or near the charging site). In response to detection of off-gas in the air samples, or if a concentration of off-gas in the air samples exceeds a threshold concentration, the controller may initiate one or more responsive actions (e.g., disabling charging functions, activating a fire suppression system, etc.).

Advantageously, the systems and methods described herein provide an approach to monitor off-gases of batteries in an uncontrolled environment. This can reduce significant costs associated with installing an off-gas detector in every mobile equipment or with modifying the environment to provide a controlled space.

Work Area and Mobile Equipment

Figure 1:
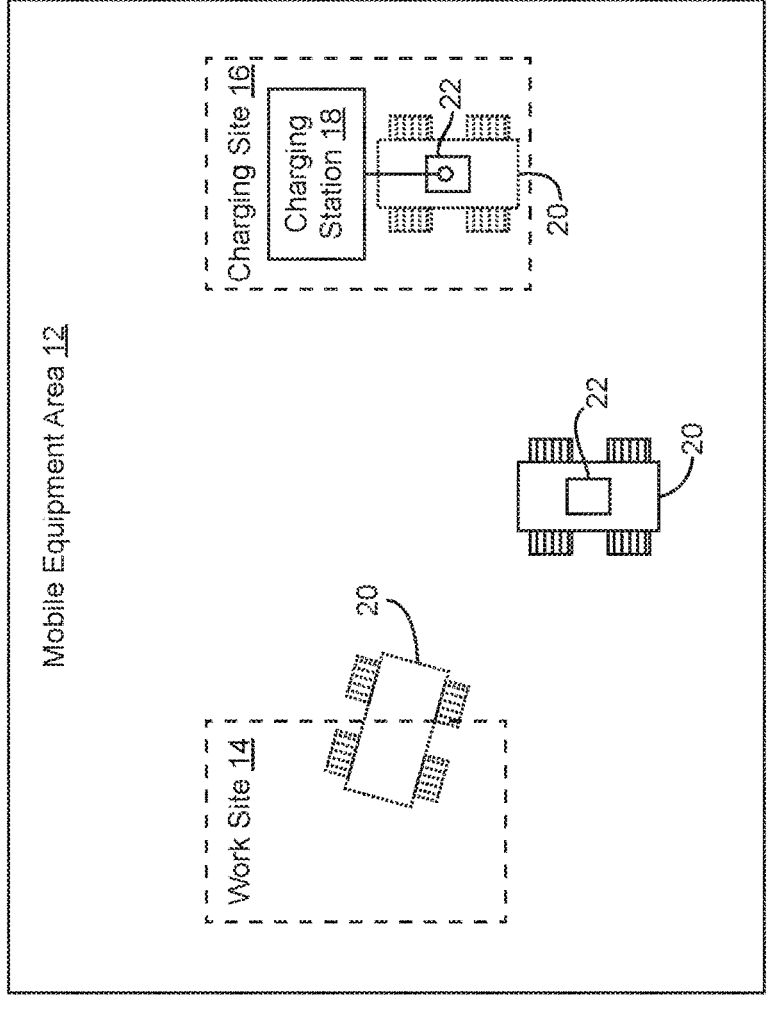
FIG. 1 is diagram of a work area including mobile equipment that can transport between a work site and a charging site, according to some embodiments.
Figure 1:

Referring particularly to FIG. 1, a work area 10 can include a mobile equipment area 12. Mobile equipment area

12 may be a portion of work area 10, or a designated zone, space, or area where mobile equipment 20 may transport, operate, or work. For example, mobile equipment area 12 may be a mining tunnel, a warehouse, a factory floor, etc., or any other environment where mobile equipment 20 may transport, operate, or work. Mobile equipment 20 may be robotic equipment, transportable equipment, a telehandler, a remote controlled mobile equipment, etc., or any machine, device, equipment, etc., that can operate and transport throughout mobile equipment area 12 (e.g., for industrial or work-related tasks). Mobile equipment 20 may be autonomous robots, remote controlled robots, etc., that operate to perform various tasks. Mobile equipment 20 can include an electrical energy storage device 22 and electric powered equipment (e.g., including an electric motor that is configured to facilitate transport of the mobile equipment 20 and/or performance of one or more work-related tasks). In some embodiments, mobile equipment 20 is operated by an operator (e.g., in an operator cab of the mobile equipment 20). Mobile equipment 20 may be an electrically powered mobile equipment that uses electrical energy from the electrical energy storage device 22 for performing its respective tasks and functions. In some embodiments, mobile equipment 20 is an electric vehicle (e.g., a car, mining equipment, etc.) that is configured to electrically couple with a charging station (e.g., charging station 18).

In some embodiments, mobile equipment area 12 includes a work site 14 and a charging site 16. It should be understood that while mobile equipment area 12 is shown to include only one work site 14 and one charging site 16, mobile equipment area 12 may include any number of work sites 14 and/or any number of charging sites 16. Likewise, mobile equipment area 12 can be served by multiple mobile equipment 20 (e.g., several mobile equipment 20 that independently operate to perform various work-related tasks).

When mobile equipment 20 operates to perform various work related tasks, mobile equipment 20 may transport or translate throughout mobile equipment area 12. In some embodiments, mobile equipment 20 may transport between various work sites 14 in mobile equipment area 12. Mobile equipment 20 uses electrical energy stored in electrical energy storage device 22 to power an electric motor that facilitates the transport of mobile equipment 20 throughout mobile equipment area 12.

After a period of use of the mobile equipment 20 (e.g., to perform various tasks, to move between areas, etc.), a charge level of the electrical energy storage device 22 may decrease. When the charge level of the electrical energy storage device 22 decreases to a point that the electrical energy storage device 22 should be recharged or replenished, the mobile equipment 20 may transport to the charging site 16 where the mobile equipment 20 may be connected to a charging station 18. The charging station 18 may provide electrical energy to the electrical energy storage device 22 of mobile equipment 20 to replenish the charge levels of the electrical energy storage device 22. The charging station 18 may draw power from a main power source (e.g., a wall power source), independent batteries, etc., or any other power source.

When mobile equipment 20 is being charged (e.g., so that it can return to service in performance of work-related tasks), mobile equipment 20 may be considered "down" by a site manager. Accordingly, any time that mobile equipment 20 spends charging is time that mobile equipment 20 is not actively able to be utilized to, for example, perform work-related tasks. In order to address this, the charging station 18 may charge mobile equipment 20 rapidly so that the mobile equipment 20 can return to performing work-related tasks. However, when the electrical energy storage device 22 is charged rapidly, this may increase a likelihood of battery failure. When a battery fails during charging, the battery may first emit specific gases (e.g., electrolyte gases), such as a lithium-ion battery off-gas, carbon dioxide, carbon monoxide, methane, ethane, hydrogen, oxygen, nitrogen oxides, volatile organic compounds, ash, soot, hydrogen sulfide, sulfur oxides, ammonia, chlorine, propane, ozone, ethanol, hydrocarbons, hydrogen cyanide, combustible gases, flammable gases, toxic gases, corrosive gases, oxidizing gases, an electrolyte vapor, etc. The emission of off-gases may indicate that the electrical energy storage device 22, or that cells of the electrical energy storage device 22 are about to experience thermal runaway and that charging should be stopped or other responsive actions performed.

Charging Station

Figure 2:
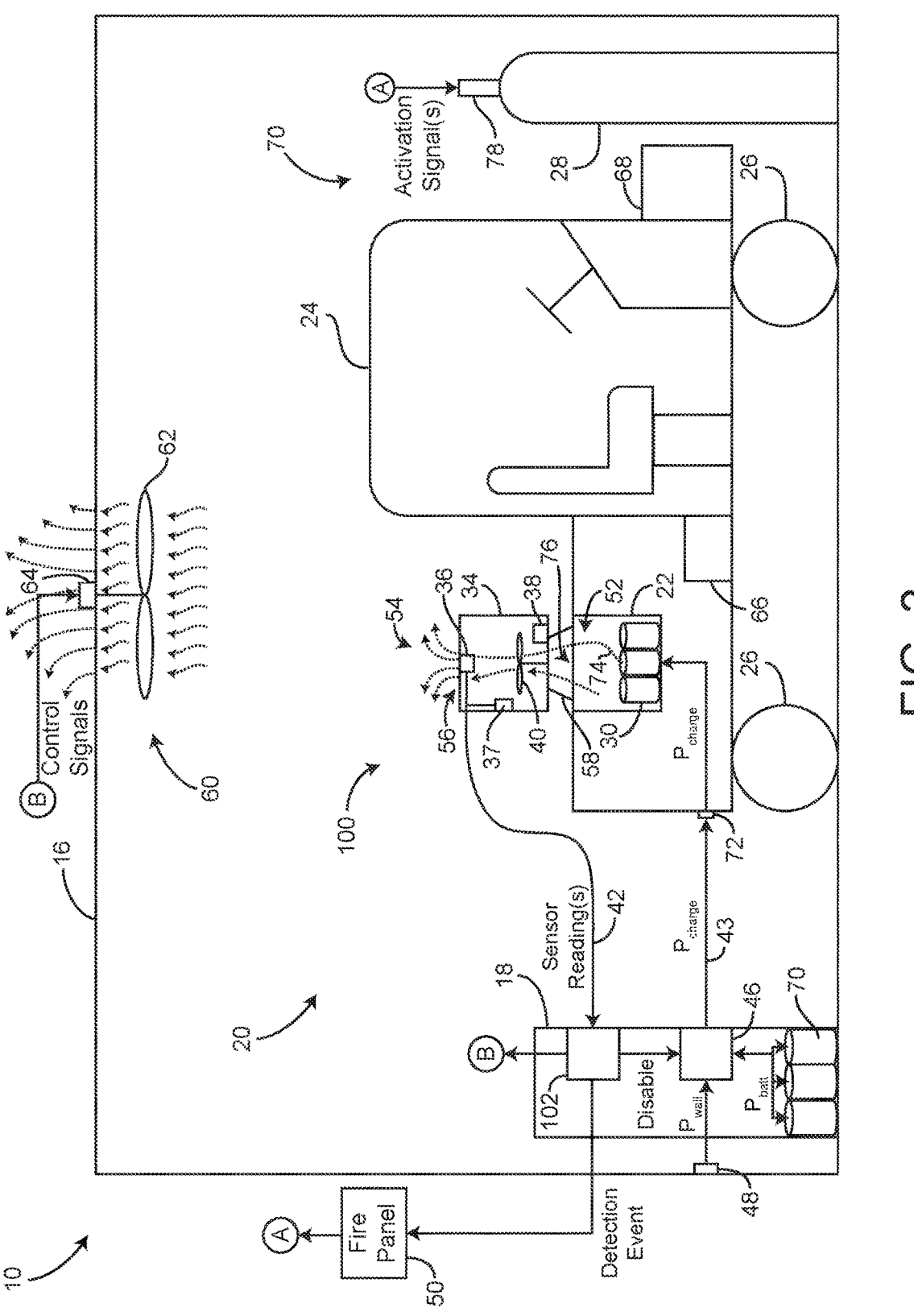
FIG. 2 is a diagram of the mobile equipment of FIG. 1 at the charging site, connected to a charging station, including an off-gas detection system, according to some embodiments.

Referring now to FIG. 2, charging site 16 is shown in greater detail, according to an exemplary embodiment. Charging site 16 includes the charging station 18, which can removably connect with electrical energy storage device 22. FIG. 2 also shows mobile equipment 20 in greater detail, according to some embodiments.

Mobile equipment 20 can include an operator cab 24 that includes one or more controls (e.g., a steering wheel, a steering device, joysticks, buttons, etc.) for controlling mobile equipment 20. Mobile equipment 20 can also include electrical energy storage device 22 that includes one or more battery cells 30. Battery cells 30 may be Lithium-Ion battery cells, or any other type of battery cell that is configured to store, discharge, or charge electrical energy. Mobile equipment 20 also includes tractive elements 26 and a primary mover 66. The primary mover 66 can be an electric motor that is configured to drive the tractive elements 26 to facilitate transport of the mobile equipment 20 throughout mobile equipment area 12. In some embodiments, mobile equipment 20 also includes an accessory feature 68 (e.g., an articulated arm, a telehandler arm, a fork attachment, a mining apparatus, etc.). Accessory feature 68 may also be configured to consume electrical energy from the electrical energy storage device 22 to perform its respective functions.

When mobile equipment 20 returns to the charging site 16 for charging at the charging station 18, electrical energy storage device 22 may be connected to the charging station 18 through a charging cable 43 at a connection point 72. Charging station 18 includes a charger 46 that is configured to draw wall power $P_{wall}$ from outlet 48 and/or battery power $P_{batt}$ from battery cells 30 and use the wall power $P_{wall}$ and/or the battery power $P_{batt}$ to charge the battery cells 30 of electrical energy storage device 22 of mobile equipment 20. For example, charger 46 may provide a charging power $P_{charge}$ to electrical energy storage device 22 to charge the battery cells 30.

Charging station 18 facilitates the charging of electrical energy storage device 22, according to some embodiments. In some embodiments, charging station 18 is usable with or configured for use with an off-gas detection system 100. Off-gas detection system 100 includes a controller 102, and an off-gas detection device 34. In some embodiments, controller 102 is positioned within charging station 18. In some embodiments, off-gas detection device 34 is a modular unit that is removably coupleable with the electrical energy storage device 22 of mobile equipment 20. For example, when electrical energy storage device 22 of mobile equipment 20 is connected with charging station 18, off-gas detection device 34 can be removably attached or coupled with electrical energy storage device 22.

Off-gas detection device 34 may be positioned above or proximate electrical energy storage device 22 to capture any emitted off-gases 52 from battery cells 30. In some embodiments, off-gas detection device 34 is configured to define a path 74 between the battery cells 30 and an off-gas detector 36 of off-gas detection device 34. Off-gas detector 36 may be configured to obtain air samples from along the path 74.

In some embodiments, charging site 16 is an uncontrolled environment, with different uncontrolled airflows. This can make obtaining concentrated air samples from the battery cells 30 difficult, since mere atmospheric air samples are not necessarily representative of the emission of off-gas from battery cells 30. However, off-gas detection device 34 can facilitate defining flow path 74 between battery cells 30 and off-gas detector 36. Advantageously, off-gas detection device 34 facilitates providing a controlled flow path between battery cells 30 and off-gas detector 36 so that sufficiently concentrated or useful air samples can be obtained in an uncontrolled environment.

Off-gas detection device 34 can include a hood, a channel, a funnel, a flow direction device, a structure, etc., shown as hood 58. Hood 58 guides air or off-gas emitted from battery cells 30 along flow path 74 and facilitates defining flow path 74. Hood 58 may be a structure that is configured to attach, couple, secure with, etc., a corresponding portion of mobile equipment 20 above an opening or vent 76 of mobile equipment 20. The hood 58 may be a converging structure to guide off-gasses into an interior or inner volume of off-gas detection device 34 (e.g., through an opening in a housing of the off-gas detection device 34). In some embodiments, hood 58 is optional and off-gas detection device 34 is directly coupled to electrical energy storage device 22 to capture off-gasses 52 that are emitted by battery cells 30 and that pass through the vent 76. Off-gas detector 36 is positioned along the flow path 74 or within the inner volume of off-gas detection device 34 so that off-gas detector 36 can obtain sensor readings regarding a concentration of off-gas in air samples that are obtained from within the inner volume of off-gas detection device 34 or from along flow path 74.

In some embodiments, off-gas detection device 34 includes components or an apparatus to actively force an airflow along the flow path 74. For example, off-gas detection device 34 may include a fan 40 and an electric motor 38 that operate to draw air out of the electrical energy storage device 22, along the flow path 74, and to the off-gas detector 36. In some embodiments, off-gas detection device 34 includes a vent 56 positioned at an outlet or an end of the flow path 74 so that exhaust gases 54 can be expelled through the vent 56. In some embodiments, the fan 40 and the electric motor 38 operate to force airflow out of the off-gas detection device 34 through the vent 56.

The off-gas detector 36 senses a concentration of presence of off-gases in air samples that are obtained from within the inner volume of off-gas detection device 34 or from along the flow path 74 and provides sensor reading(s) to controller 102. In some embodiments, the off-gas detector 36 is electrically or communicably coupled with controller 102 through a cable 42. In some embodiments, cable 42 and the charging cable 43 are a single cable or are bundled as a single cable. In other embodiments, controller 102 communicates wirelessly with off-gas detector 36 when off-gas detector 36 is in proximity of controller 102 (e.g., using Bluetooth, LoRa, Zigbee, etc., or any other wireless communications technique). Controller 102 can use the sensor reading(s) (e.g., concentration or presence of off-gas) to determine one or more responsive actions. In some embodiments, controller 102 uses the sensor reading(s) to determine if the battery cells 30 are experiencing thermal runaway. Controller 102 may initiate various actions such as disabling charging operations of charger 46, providing a detection event to a fire panel 50, providing activation signals to a fire suppression system 70, or providing control signals to a ventilation system 60 of charging site 16. Similarly, controller 102 can be configured to receive temperature or sensor reading(s) from a temperature sensor 37 of off-gas detection device 34

As shown in FIG. 2, charging site 16 may also include ventilation system 60. In some embodiments, ventilation system 60 is a controllable ventilation system including a fan 62 and an electric motor 64 configured to drive the fan 62. Controller 102 can generate and provide control signals to ventilation system 60 to activate or adjust a ventilation rate at charging site 16 (e.g., in response to detecting that battery cells 30 have emitted off-gas, or in response to detecting thermal runaway).

As shown in FIG. 2, charging site 16 may also include fire suppression system 70. Fire suppression system 70 can include a canister 28 that stores a pressurized fire suppressant agent (e.g., an inert gas). In some embodiments, the canister 28 includes an actuatable nozzle 78 that is configured to actuate between a closed position and an open position when activated. Once activated (e.g., in response to receiving activation signals from the controller 102), the nozzle 78 transitions into the open configuration or position and the fire suppressant agent is provided to charging site 16.

Advantageously, off-gas detection system 100 provides a plug-and-play approach to apply off-gas detection in an uncontrolled environment. The off-gas detection device 34 can be removably coupled with the electrical energy storage device 22 to define a controlled flow path between battery cells 30 and off-gas detector 36 in an otherwise uncontrolled environment. This facilitates the detection of off-gases and thermal runaway.

In some embodiments, the charging cable 43 is integrated with the off-gas detection device 34 so that the off-gas detection device 34 and the charging cable 43 can be simultaneously connected or coupled. In some embodiments, the connection point 72 is at a location proximate the battery cells 30 or the electrical energy storage device 22 so that the off-gas detection device 34 can both be physically coupled with the mobile equipment 20 and electrically coupled with the charging station 18.

In some embodiments, the electrical energy storage device 22 is provided as an integral component of the mobile equipment 20. In some embodiments, the electrical energy storage device 22 is removably coupled with the mobile equipment 20 and can be removed from the mobile equipment 20. When the electrical energy storage device 22 is removed from the mobile equipment 20, the off-gas detection device 34 can be placed on top of, coupled with, etc., the electrical energy storage device 22 even when the electrical energy storage device 22 is not on-board the mobile equipment 20. The removed electrical energy storage device 22 can also be electrically coupled with the charging station 18 when removed from the mobile equipment 20. Advantageously, the mobile equipment 20 may arrive at the charging station 18, the electrical energy storage device 22 can be removed, electrically coupled with the charging station 18 and physically coupled with the off-gas detection device 34, and a new or fully charged electrical energy storage device 22 can be installed in the mobile equipment 20 so that mobile equipment can be operated while the previously installed or depleted electrical energy storage device 22 is charged by the charging station 18 and monitored by the off-gas detection device 34.
Controller Referring particularly to FIG. 3, a portion of off-gas detection system 100 is shown in greater detail, according to some embodiments. Specifically, controller 102 is shown in greater detail, according to some embodiments. Controller 102 includes a processing circuit 304 including a processor 306 and memory 308. Processor 306 may be a general purpose or specific purpose processor, an application specific integrated circuit (ASIC), one or more field programmable gate arrays (FPGAs), a group of processing components, or other suitable processing components. Processor 306 is configured to execute computer code or instructions stored in memory 308 or received from other computer readable media (e.g., CDROM, network storage, a remote server, etc.).

Memory 308 may include one or more devices (e.g., memory units, memory devices, storage devices, etc.) for storing data and/or computer code for completing and/or facilitating the various processes described in the present disclosure. Memory 308 may include random access memory (RAM), read-only memory (ROM), hard drive storage, temporary storage, non-volatile memory, flash memory, optical memory, or any other suitable memory for storing software objects and/or computer instructions. Memory 308 may include database components, object code components, script components, or any other type of information structure for supporting the various activities and information structures described in the present disclosure. Memory 308 may be communicably connected to processor 306 via processing circuit 304 and may include computer code for executing (e.g., by processor 306) one or more processes described herein. When processor 306 executes instructions stored in memory 308, processor 306 generally configures controller 102 (and more particularly processing circuit 304) to complete such activities.

Memory 308 is shown to include an off-gas manager 310 and a response manager 312. Off-gas manager 310 is configured to receive one or more sensor reading(s) from off-gas detector 36 and/or one or more temperature reading(s) from temperature sensor 37 and perform its functionality to determine if a thermal runaway event has occurred, or to determine if a concentration of off-gas in the air samples used by off-gas detector 36 exceed a threshold concentration. Response manager 312 is configured to receive the off-gas detection or the thermal runaway detection from off-gas manager 310 and use the off-gas detection and/or the thermal runaway detection to activate or initiate one or more responsive actions.

Figure 3:
FIG. 3 is a block diagram of a controller that is configured to receive sensor feedback from a sensor of the off-gas detection system and perform or initiate one or more response actions when off-gas or thermal runaway is detected, according to some embodiments.
Figure 3:
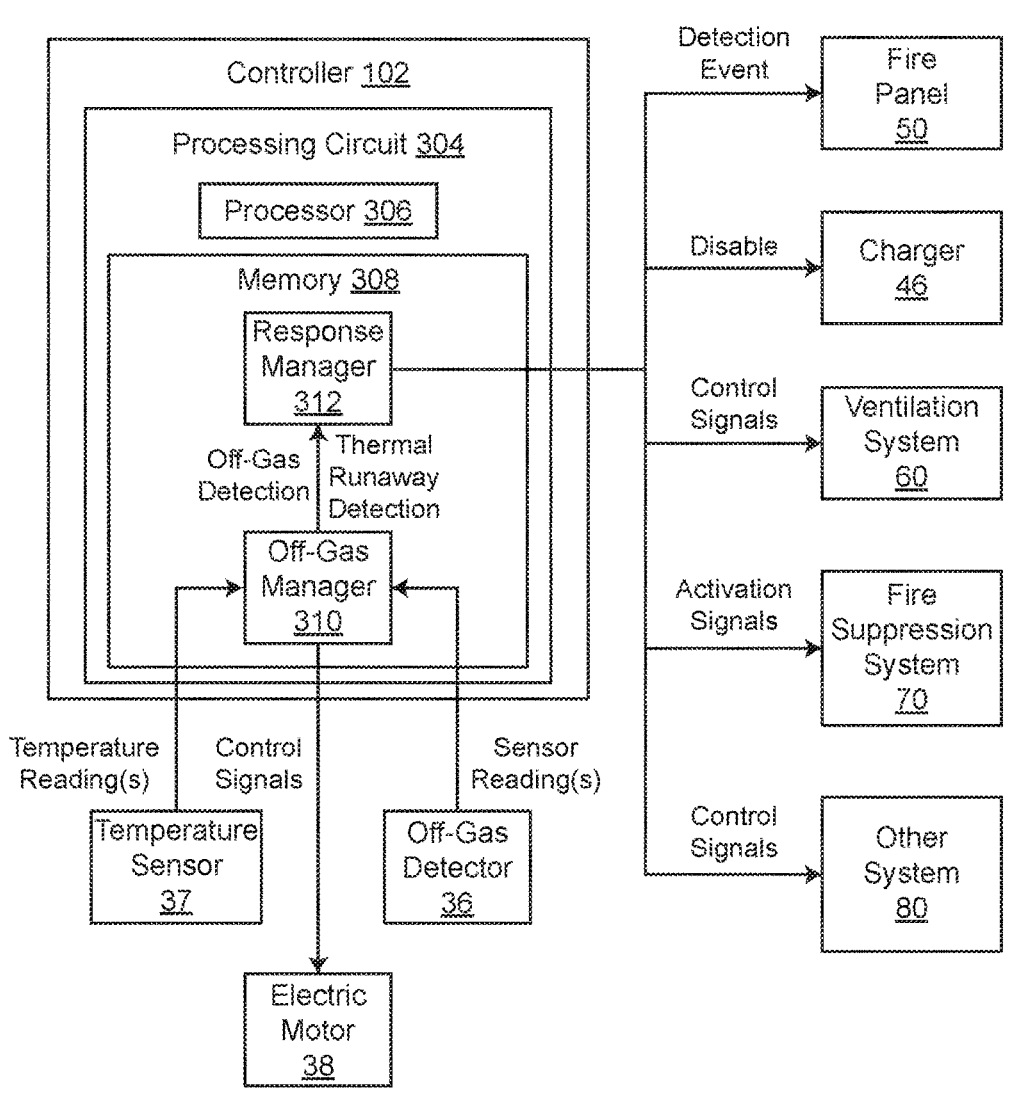

Referring still to FIG. 3, off-gas manager 310 is shown receiving the sensor reading(s) from off-gas detector 36. In some embodiments, off-gas manager 310 is configured to receive the sensor reading(s) from off-gas detector 36 and determine if off-gas is present along the flow path 74 (e.g., if off-gas is emitted by the battery cells 30). In some embodiments, off-gas manager 310 provides response manager 312 with an indication of whether or not off-gas is present/detected.

In some embodiments, off-gas manager 310 is configured to use the sensor reading(s) received from off-gas detector 36 to identify a concentration of off-gas along the flow path 74. For example, off-gas manager 310 can determine a concentration C of the off-gas that is emitted by the battery cells 30. In some embodiments, the concentrations have values of parts per million (e.g., C=off-gas ppm), a ratio of a volume $V_{gas}$ of the detected off-gas to the volume of the air sample $V_{sample}$ $$(e.g., C_j = \frac{V_{gas,j}}{V_{sample}}),$$

a ratio of a mass $m_{gas}$ of the detected off-gas to mass of the air sample $m_{sample}$ $$(e.g., C_j = \frac{m_{gas,j}}{m_{sample}}),$$

etc. In some embodiments, the concentration indicates a ratio of an amount of the off-gas in the sample to the total amount of the air sample.

In some embodiments, off-gas manager 310 provides any of the concentration C to response manager 312. Off-gas manager 310 can be configured to generate control signals for electric motor 38 (e.g., for the fan 40) to draw air samples to the off-gas detector 36 along flow path 74.

Referring still to FIG. 3, response manager 312 can receive the off-gas concentration, the off-gas detection, or thermal runaway detection from off-gas manager 310. In some embodiments, response manager 312 is configured to analyze the off-gas concentrations to identify if a fire is likely to occur in the near-future at the electrical energy storage device 22. Response manager 312 can receive the concentration from off-gas manager 310 and compare the concentration to a threshold concentration value $C_{threshold}$. In some embodiments, the threshold concentration value $C_{threshold}$ is a predetermined value that indicates whether a significant amount of off-gas are present in the air sample. In some embodiments, $C_{threshold}$ is equal to zero or substantially equal to zero, such that response manager 312 determines that a fire is likely to occur at electrical energy storage device 22 in response to any amount of off-gas being detected in electrical energy storage device 22.

In response to the concentration C exceeding the threshold concentration value $C_{threshold}$, response manager 312 can determine that a fire is likely to occur in the near future at the electrical energy storage device 22. In response to determining that a fire is likely to occur in the near future at the electrical energy storage device 22, response manager 312 can generate activation signals (e.g., fire suppression release signals) and provide the activation signals to fire suppression system 70 to activate fire suppression system 70 and discharge the fire suppression agent to suppress or prevent the fire from occurring. If the concentration of off-gas in the air sample or along the flow path 74 does not exceed the threshold concentration value $C_{threshold}$, response manager 312 does not activate fire suppression system 70 and continues periodically checking the concentrations of off-gas as provided by off-gas manager 310.

In some embodiments, off-gas manager 310 is configured to receive temperature signals from temperature sensor 37. Off-gas manager 310 can use the temperature at the electrical energy storage device 22 to determine if a fire has occurred or is likely to occur. Off-gas manager 310 or response manager 312 can compare the temperature at the electrical energy storage device 22 to a corresponding threshold temperature to determine if a fire has occurred or if a fire is likely to occur in the near future. In some embodiments, response manager 312 initiates or activates one or more responsive actions (e.g., activating fire suppression system 70) in response to the temperature at the electrical energy storage device 22 exceeding the threshold temperature value.

In some embodiments, off-gas manager 310 receives sensed temperature values associated with the electrical energy storage device 22 (e.g., as electrical energy storage device 22 is being charged) from temperature sensor 37. Off-gas manager 310 can determine a rate of change of the temperature $\dot{T}$ over time. In some embodiments, if the rate of change of the temperature $\dot{T}$ exceeds a corresponding temperature rate of change threshold value $\dot{T}_{threshold}$ for a predetermined time duration $\Delta t$, off-gas manager 310 may determine that a fire is likely to occur at the electrical energy storage device 22 and initiate or activate one or more responsive actions (e.g., activating fire suppression system 70) to respond to the imminent fire event. In some embodiments, the rate of change of the temperature $\dot{T}$ exceeding the corresponding temperature rate of change threshold value $\dot{T}_{threshold}$ indicates that the electrical energy storage device 22 is experiencing or is about to experience thermal runaway. In response to determining that the electrical energy storage device 22 is experiencing thermal runaway or is about to experience thermal runaway, off-gas manager 310 can provide a thermal runaway detection to response manager 312.

In this way, off-gas manager 310 and response manager 312 can use the off-gas concentrations and temperature to preemptively initiate or activate a responsive action (e.g., to activate fire suppression system 70 to prevent a fire from occurring at electrical energy storage device 22 or to suppress a fire at electrical energy storage device 22). In some embodiments, off-gas detection device 34 also includes an optical sensor configured to measure heat or light emitted by a fire. In this way, off-gas manager 310 and/or response manager 312 can receive sensor data from the optical sensor and use the sensor data to determine if a fire has occurred.

In response to off-gas detection or thermal runaway detection, response manager 312 can initiate or activate one or more responsive actions to address the fire or the potential fire. For example, response manager 312 may provide a detection event to fire panel 50. The detection event may include an indication that the battery cells 30 of the electrical energy storage device 22 are emitting off-gas or that the battery cells 30 are experiencing thermal runaway. The fire panel 50 may notify personnel, activate a fire alarm, etc., or take other actions in response to receiving the detection event.

In some embodiments, response manager 312 is configured to provide a disable command to charger 46. For example, if response manager 312 identifies that off-gas has been emitted by the battery cells 30 or that the battery cells 30 are experiencing thermal runaway, response manager 312 may disable or stop the charger 46 from charging the electrical energy storage device 22. Charger 46 may receive the disable command and stop providing the charge power $P_{charge}$ to the battery cells 30.

In some embodiments, response manager 312 is configured to provide control signals to ventilation system 60 (e.g., to electric motor 64). Response manager 312 may provide the control signals to ventilation system 60 in response to receiving the off-gas detection or the thermal runaway detection from off-gas manager 310. In some embodiments, response manager 312 is configured to adjust the control signals (e.g., to achieve a different ventilation rate) in response to receiving the off-gas detection or the thermal runaway detection from the off-gas manager 310.

In some embodiments, response manager 312 is configured to activate fire suppression system 70 in response to receiving the off-gas detection or the thermal runaway detection from off-gas manager 310. For example, response manager 312 may activate the fire suppression system 70 to suppress or prevent a fire from occurring at the electrical energy storage device 22.

In some embodiments, response manager 312 is configured to generate and provide control signals to another system 80 of charging site 16. For example, charging site 16 may include actuators that are configured to operate to raise or lower curtains to produce a controlled environment at charging site 16. In response to receiving the off-gas detection or the thermal runaway detection, response manager 312 may provide the control signals to the other system 80 (e.g., to lower the curtains and produce a controlled environment at charging site 16).

In some embodiments, response manager 312 is configured to perform or initiate one or more of the responsive actions in response to receiving the off-gas detection or the thermal runaway detection. For example, response manager 312 may perform all of the illustrated responsive actions, or only some of them. For example, response manager 312 may disable the charging of battery cells 30 while notifying the fire panel, and increasing ventilation.

Process

Referring particularly to FIG. 4, a process 400 for detecting off-gas of one or more battery cells that are being charged is shown, according to some embodiments. Process 400 includes steps 402-416 and can be performed to monitor a battery health or status (e.g., through the detection of off-gas).

Process 400 includes transporting mobile equipment to a charging site (step 402), according to some embodiments. In some embodiments, the mobile equipment is autonomous or user operated equipment (e.g., including an operator cab or a remotely controlled equipment). The mobile equipment can include tractive elements (e.g., wheels, treads, etc.) that are driven by an electric motor which draws electrical energy from an electrical energy storage device (e.g., a capacitor, a battery, etc.). The electrical energy storage device may be stored or located on-board the mobile equipment. In some embodiments, the mobile equipment is configured to transport from one location to another (e.g., from a work site to a charging site or a charging station).

Process 400 includes removably connecting an off-gas detection device to the mobile equipment proximate an electrical energy storage device of the mobile equipment to define a controlled flow path between the electrical energy storage device and an off-gas detector (step 404), according to some embodiments. Step 404 can be performed automatically or by a user when the mobile equipment transports to the charging site. Step 404 may include removably coupling (e.g., with fasteners) the off-gas detection device to the mobile equipment proximate (e.g., above) so that the controlled flow path can be defined. In some embodiments, the charging site is an uncontrolled environment which can make obtaining air samples for off gas detection difficult. However, the controlled flow path facilitates transmitting air samples from battery cells of the electrical energy storage device to the off-gas detector for detection despite the uncontrolled environment. In some embodiments, step 404 includes connecting or coupling off-gas detection device 34 with electrical energy storage device 22. Step 404 can also include connecting cable 42 between off-gas detector 36 and temperature sensor 37 and controller 102.

Process 400 includes electrically connecting the electrical energy storage device of the mobile equipment with a charging station at the charging site (step 406), according to some embodiments. In some embodiments, step 406 includes connecting the electrical energy storage device of the mobile equipment with a charging station at the charging site via cable 43. The charging station may include a charger that draws electrical energy from a main power source to charge the electrical energy storage device.

Process 400 includes operating the charging station to charge the electrical energy device (step 408), according to some embodiments. Step 408 can include drawing power at a charger of the charging station from a main power source and providing charge power to the electrical energy storage device 22. In some embodiments, step 408 is performed by charger 46 and controller 102.

Process 400 includes operating a fan to drive airflow along the controlled flow path from the electrical energy storage device to the off-gas detector (step 410), according to some embodiments. In some embodiments, step 410 is optional. In some embodiments, step 410 is performed by electric motor 38 and fan 40 based on control signals received from controller 102.

Process 400 includes detecting a presence of off-gas in air samples obtained from along the controlled flow path using the off-gas detector (step 412), according to some embodiments. In some embodiments, step 412 is performed by off-gas detector 36. Off-gas detector 36 can obtain air samples that include any off-gases emitted by the battery cells 30 of electrical energy storage device 22. The off-gas detector 36 may provide sensor reading(s) to the controller 102. Step 412 can also be performed by controller 102, or more particularly, by off-gas manager 310, based on the sensor reading(s) obtained from the off-gas detector 36.

Process 400 includes performing one or more responsive actions in response to detecting the presence of off-gas in the air samples (step 414), according to some embodiments. In some embodiments, the one or more responsive actions are activated or initiated by controller 102, or more particularly, by response manager 312, in response to off-gas detection or thermal runaway detection. For example, response manager 312 may provide a detection event to a fire panel (e.g., fire panel 50), a disable command to the charger 46, control signals to ventilation system 60, activation signals to fire suppression system 70, or control signals to another system 80. The responsive actions may be initiated to suppress a potential or actual fire or to preemptively suppress fire.

Process 400 includes providing a shut-off or disable command to the charging station to stop charging the electrical energy storage device in response to detecting the presence of off-gas in the air samples obtained from along the controlled flow path (step 416), according to some embodiments. Step 416 can be performed by response manager 312 and charger 46. Advantageously, if the battery cells 30 are beginning to emit off-gas, charging may be ceased to reduce a likelihood of battery failure.

Configuration of Exemplary Embodiments

As utilized herein, the terms "approximately," "about," "substantially," and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described and claimed without restricting the scope of these features to the precise numerical ranges provided. Accordingly, these terms should be interpreted as indicating that insubstantial or inconsequential modifications or alterations of the subject matter described and claimed are considered to be within the scope of the disclosure as recited in the appended claims.

It should be noted that the term "exemplary" and variations thereof, as used herein to describe various embodiments, are intended to indicate that such embodiments are possible examples, representations, and/or illustrations of possible embodiments (and such terms are not intended to connote that such embodiments are necessarily extraordinary or superlative examples).

The term "coupled," as used herein, means the joining of two members directly or indirectly to one another. Such joining may be stationary (e.g., permanent or fixed) or moveable (e.g., removable or releasable). Such joining may be achieved with the two members coupled directly to each other, with the two members coupled to each other using a separate intervening member and any additional intermediate members coupled with one another, or with the two members coupled to each other using an intervening member that is integrally formed as a single unitary body with one of the two members. Such members may be coupled mechanically, electrically, and/or fluidly.

The term "or," as used herein, is used in its inclusive sense (and not in its exclusive sense) so that when used to connect a list of elements, the term "or" means one, some, or all of the elements in the list. Conjunctive language such as the phrase "at least one of X, Y, and Z," unless specifically stated otherwise, is understood to convey that an element may be either X, Y, Z; X and Y; X and Z; Y and Z; or X, Y, and Z (i.e., any combination of X, Y, and Z). Thus, such conjunctive language is not generally intended to imply that certain embodiments require at least one of X, at least one of Y, and at least one of Z to each be present, unless otherwise indicated.

References herein to the positions of elements (e.g., "top," "bottom," "above," "below," etc.) are merely used to describe the orientation of various elements in the FIGURES. It should be noted that the orientation of various elements may differ according to other exemplary embodiments, and that such variations are intended to be encompassed by the present disclosure.

The hardware and data processing components used to implement the various processes, operations, illustrative logics, logical blocks, modules and circuits described in connection with the embodiments disclosed herein may be implemented or performed with a general purpose single- or multi-chip processor, a digital signal processor (DSP), an application specific integrated circuit (ASIC), a field programmable gate array (FPGA), or other programmable logic device, discrete gate or transistor logic, discrete hardware components, or any combination thereof designed to perform the functions described herein. A general purpose processor may be a microprocessor, or, any conventional processor, controller, microcontroller, or state machine. A processor also may be implemented as a combination of computing devices, such as a combination of a DSP and a microprocessor, a plurality of microprocessors, one or more microprocessors in conjunction with a DSP core, or any other such configuration. In some embodiments, particular processes and methods may be performed by circuitry that is specific to a given function. The memory (e.g., memory, memory unit, storage device, etc.) may include one or more devices (e.g., RAM, ROM, Flash memory, hard disk storage, etc.) for storing data and/or computer code for completing or facilitating the various processes, layers and modules described in the present disclosure. The memory may be or include volatile memory or non-volatile memory, and may include database components, object code components, script components, or any other type of information structure for supporting the various activities and information structures described in the present disclosure. According to an exemplary embodiment, the memory is communicably connected to the processor via a processing circuit and includes computer code for executing (e.g., by the processing circuit and/or the processor) the one or more processes described herein.

The present disclosure contemplates methods, systems and program products on any machine-readable media for accomplishing various operations. The embodiments of the present disclosure may be implemented using existing computer processors, or by a special purpose computer processor for an appropriate system, incorporated for this or another purpose, or by a hardwired system. Embodiments within the scope of the present disclosure include program products comprising machine-readable media for carrying or having machine-executable instructions or data structures stored thereon. Such machine-readable media can be any available media that can be accessed by a general purpose or special purpose computer or other machine with a processor. By way of example, such machine-readable media can comprise RAM, ROM, EPROM, EEPROM, or other optical disk storage, magnetic disk storage or other magnetic storage devices, or any other medium which can be used to carry or store desired program code in the form of machine-executable instructions or data structures and which can be accessed by a general purpose or special purpose computer or other machine with a processor. Combinations of the above are also included within the scope of machine-readable media. Machine-executable instructions include, for example, instructions and data which cause a general purpose computer, special purpose computer, or special purpose processing machines to perform a certain function or group of functions.

Although the figures and description may illustrate a specific order of method steps, the order of such steps may differ from what is depicted and described, unless specified differently above. Also, two or more steps may be performed concurrently or with partial concurrence, unless specified differently above. Such variation may depend, for example, on the software and hardware systems chosen and on designer choice. All such variations are within the scope of the disclosure. Likewise, software implementations of the described methods could be accomplished with standard programming techniques with rule-based logic and other logic to accomplish the various connection steps, processing steps, comparison steps, and decision steps.

It is important to note that the construction and arrangement of the fire suppression system as shown in the various exemplary embodiments is illustrative only. Although only a few embodiments have been described in detail in this disclosure, many modifications are possible (e.g., variations in sizes, dimensions, structures, shapes and proportions of the various elements, values of parameters, mounting arrangements, use of materials, colors, orientations, etc.). For example, the position of elements may be reversed or otherwise varied and the nature or number of discrete elements or positions may be altered or varied. Accordingly, all such modifications are intended to be included within the scope of the present disclosure. Other substitutions, modifications, changes, and omissions may be made in the design, operating conditions and arrangement of the exemplary embodiments without departing from the scope of the present disclosure.

What is claimed is:

1. An off-gas detection system for a mobile equipment, the off-gas detection system comprising:

an off-gas detection device configured to removably couple with the mobile equipment, the off-gas detection device configured to define a controlled flow path from an electrical energy storage device of the mobile equipment to an off-gas detector; and a controller configured to:

receive data from the off-gas detector regarding an air sample;

determine a presence or concentration of off-gas within the air sample; and initiate one or more actions in response to determining the presence or concentration of off-gas in the air sample.

2. The off-gas detection system of claim 1, wherein the off-gas detection device is removably coupled with the mobile equipment proximate the electrical energy storage device of the mobile equipment.

3. The off-gas detection system of claim 1, wherein the off-gas detection system is positioned in an uncontrolled environment.

4. The off-gas detection system of claim 1, wherein the off-gas detection device further comprises a fan and an electric motor, wherein the electric motor and the fan are configured to operate to draw air along the controlled flow path from the electrical energy storage device to the off-gas detector, and wherein the controller is further configured to determine the presence or concentration of off-gas within the air sample indicates a fire is likely to occur.

5. The off-gas detection system of claim 1, wherein the one or more actions comprise at least one of:

providing detection event information to a fire panel;

disabling a charging operation of the electrical energy storage device;

operating a ventilation system; or activating a fire suppression system.

6. The off-gas detection system of claim 1, wherein the electrical energy storage device is configured to electrically couple with a charger to charge one or more battery cells of the electrical energy storage device while the off-gas detector monitors air samples from along the controlled flow path.

7. The off-gas detection system of claim 1, wherein the off-gas detection device comprises a hood configured to directly couple to the mobile device to direct air from the electrical energy storage device to the off-gas detector along the controlled flow path.

8. A method of detecting off-gas comprising:

coupling an off-gas detection device to an equipment to define an interior volume beginning at the equipment and extending to the off-gas detection device, the equipment comprising an electrical energy storage device;

coupling the equipment to a charging station to charge the electrical energy storage device;

detecting a presence or concentration of off gas in an air sample using the interior volume as a controlled air path provided by the off-gas detection device from the electrical energy storage device to the off-gas detection device; and initiating an action based on detecting the presence or concentration of the off gas.

9. The method of claim 8, wherein the off-gas detection device is coupled to the equipment proximate the electrical energy storage device.

10. The method of claim 8, wherein the equipment is positioned in an uncontrolled environment and the off-gas detection device defines the controlled air path between the electrical energy storage device and an off-gas detector.

11. The method of claim 8, further comprising:

operating a fan to force a flow of air along the controlled air path.

12. The method of claim 8, wherein the action comprises at least one of:

providing detection event information to a fire panel;

disabling a charging operation of the electrical energy storage device;

operating a ventilation system; or activating a fire suppression system.

13. The method of claim 8, wherein the equipment is at least one of:

a battery module on-board a vehicle;

a battery module removed from a vehicle; or a mobile vehicle.

14. An off-gas detection device for an equipment comprising:

an off-gas detector; and a body configured to define a channel for a controlled flow path directly from an electrical energy storage device of the equipment to the off-gas detector;

wherein the off-gas detection device is configured to removably couple with the equipment or the electrical energy storage device of the equipment so that the controlled flow path is defined between the electrical energy storage device of the equipment and the off-gas detector;

wherein the off-gas detector is configured to provide sensor data to a controller for limiting charging of the electrical energy storage device in response to the sensor data.

15. The off-gas detection device of claim 14, wherein the off-gas detection device is configured to be removably coupled with the equipment proximate the electrical energy storage device of the equipment.

16. The off-gas detection device of claim 14, wherein the off-gas detection device further comprises a fan and an electric motor, wherein the electric motor and the fan are configured to operate to draw air along the controlled flow path from the electrical energy storage device to the off-gas detector.

17. The off-gas detection device of claim 14, wherein the electrical energy storage device is configured to electrically couple with a charger to charge one or more battery cells of the electrical energy storage device while the off-gas detector monitors air samples from along the controlled flow path.

18. The off-gas detection device of claim 17, wherein a connection point between the charger and the electrical energy storage device is integrated in the off-gas detection device.

19. The off-gas detection device of claim 14, further comprising a temperature sensor, wherein the temperature sensor is configured to monitor a temperature of the electrical energy storage device and provide the monitored temperature to the controller for use in limiting charging of the electrical energy storage device.

20. The off-gas detection device of claim 14, wherein the equipment is at least one of:

a battery module on-board a vehicle;

a battery module removed from a vehicle; or a mobile vehicle.

\* \* \* \* \*